United States Patent [19]

Lee

[11] Patent Number: 5,431,153
[45] Date of Patent: Jul. 11, 1995

[54] SURGICAL APPARATUS FOR ASSISTING IN THE RELEASE OF THE CARPAL TUNNEL

[76] Inventor: Hans Lee, Suite 200, 415 Morris St., Charleston, W. Va. 25301

[21] Appl. No.: 74,521

[22] Filed: Jun. 11, 1993

[51] Int. Cl.⁶ .............................................. A61B 17/00
[52] U.S. Cl. ...................................... 600/183; 606/191
[58] Field of Search ............... 128/20, 17, 18, 3, 15, 128/10, 11, 13, 16; 606/191, 190, 198, 170

[56] References Cited

U.S. PATENT DOCUMENTS

| | | | |
|---|---|---|---|
| 2,829,649 | 5/1958 | Glenner | 128/20 |
| 3,581,376 | 6/1971 | Pilling . | |
| 3,641,332 | 2/1972 | Reick et al. . | |
| 3,826,248 | 7/1974 | Gobels . | |
| 3,986,854 | 10/1976 | Scrivo et al. | 128/11 |
| 4,052,980 | 10/1977 | Grams et al. . | |
| 4,226,228 | 10/1980 | Shin et al. . | |
| 4,337,763 | 7/1982 | Petrassevich . | |
| 4,562,832 | 1/1986 | Wilder et al. | 128/20 |
| 4,597,030 | 6/1986 | Brody et al. . | |
| 5,029,573 | 7/1991 | Chow | 606/170 X |
| 5,065,738 | 11/1991 | Van Dam | 128/11 |
| 5,269,796 | 12/1993 | Miller et al. | 606/167 |
| 5,273,024 | 12/1993 | Menon et al. | 128/4 |

FOREIGN PATENT DOCUMENTS

| | | | |
|---|---|---|---|
| 0517608 | 12/1992 | European Pat. Off. | 128/20 |
| 3314787 | 10/1984 | Germany | 128/3 |
| 3934804 | 4/1991 | Germany | 128/10 |
| 2078526 | 1/1982 | United Kingdom | 128/20 |

OTHER PUBLICATIONS

"Improved Suspension Laryngoscope for Use with Operative Microscope" Woodrow, p. 412, 1970.
"Ideas and Innovations", Devine et al, Plastic and Reconstructive Surgery, 1971, p. 90.

*Primary Examiner*—Richard J. Apley
*Assistant Examiner*—Donna L. Maraglio
*Attorney, Agent, or Firm*—Lowe, Price, LeBlanc & Becker

[57] ABSTRACT

A surgical retractor for exposing a carpal ligament through a small transverse incision along the wrist, comprising a blade having an arch-shaped configuration in cross-section which arch becomes generally flat at a tip section thereof, said tip being tapered in plan view and adapted to be initially inserted through the incision to facilitate advancement of the blade along a plane between the ligament and overlying skin and tissue and muscle structures to thereby progressively expose the ligament by distal retraction; and a light conduit extending through the arch of the blade and terminating in spaced relation to the tip to project light toward the tip to illuminate the area being distally retracted between the tip and conduit. A surgical method employing the novel retractor of this invention is also disclosed.

9 Claims, 6 Drawing Sheets

SURGICAL APPARATUS FOR ASSISTING IN THE RELEASE OF THE CARPAL TUNNEL

TECHNICAL FIELD

The present invention relates generally to the surgical treatment of carpal tunnel syndrome and, more particularly, to surgical apparatus and methods of splitting the transverse carpal ligament to decompress the carpal tunnel.

BACKGROUND ART

Carpal tunnel syndrome is a clinical condition brought upon by a compressed or pinched median nerve at the wrist. Usual symptoms of this condition are numbness, tingling and pain in the hand, fingers and arm. This occurs when pressure builds up within the tunnel for various reasons, such as swelling of the lining tissue of the tendons, fracture, dislocation or arthritis of the wrist, all of which compresses the median nerve which causes carpal tunnel syndrome. The carpal tunnel is a narrow channel through which nine flexor tendons and the median nerve pass. The dorsal floor (base) of the tunnel is formed by a concave arch of carpal bones covered by intrinsic and extrinsic palmar wrist ligaments. The roof of the tunnel is formed by a transverse carpal ligament which is about 2-3 mm thick, 3-4 cm wide and approximately 3-4 cm long. This ligament is rigid and does not stretch and the treatment of this condition is usually and initially conservative, i.e., rest, splint, and medication.

When the symptoms are severe and constant and if the patient fails to respond to the aforementioned conservative treatment, surgical intervention is necessary. The surgery involves the release (splitting) of the transverse carpal ligament in the vertical (up and down or along the longitudinal axis of the hand) direction which in turn decompresses the tunnel. To achieve release of the transverse carpal ligament, an incision is made in the skin on the palmar aspect of the wrist, or can be made in the vertical direction (i.e., longitudinal) on the hand, or some modification of a vertical incision can be made to expose the ligament, followed by cutting of the ligament as mentioned above.

When the incision is made in the vertical or longitudinal direction on the palmar aspect of the hand, the resulting complete exposure of the transverse carpal ligament ensures easy splitting or cutting of the ligament with minimal risk of damaging the nerves, blood vessels, or obtaining incomplete release of the ligament. However, when the incision heals, there is extensive scar tissue which is both unsightly and painful and may impair full recovery of hand function. When the incision is made transversely along the skin crease of the wrist, there are advantages such as rapid healing, shorter recovery time, and excellent scar formation following surgery. However, there are also disadvantages resulting from poor exposure of the ligament during the surgical procedure which can then, during cutting, increase the risk of damaging the nerves, blood vessels, while possibly obtaining incomplete release of the ligament.

The trend in this surgery is to search for a means of achieving better exposure of the ligament through a small transverse incision and, as such, a procedure known as endoscopic release of the carpal tunnel is becoming popular. In this approach, there is utilized a scope which is a rigid tube having a lens at one end through which view of the surgical field is being transmitted into the TV monitor for surgeons observation, followed by cutting of the carpal ligament with a special knife contained in the tube. However, this approach does not provide adequate exposure of the median nerve which in turn increases the risk of potential damage to the nerve or its branches. Also, additional training of the surgeon is necessary to perform the endoscopic release. The procedure itself is time consuming and, furthermore, the setup for the endoscopic carpal tunnel approach is quite expensive. Finally, the use of a special kit (i.e., special knife and dissector, etc.) is required for each patient which is therefore costly.

It is accordingly one object of the present invention to obtain complete release of the carpal ligament while avoiding damage to the median nerve or its branches.

Another object is to completely release the carpal tunnel ligament through a small transverse incision and without either a vertical incision or utilization of an endoscopic approach.

Another object is to provide surgical equipment and method of use without requiring substantial additional training of the surgeon and without requiring expensive special equipment.

Still another object is to obtain complete release of the carpal ligament through a small transverse incision using equipment which does not require elaborate and time consuming setup.

DISCLOSURE OF THE INVENTION

A surgical retractor for exposing a carpal ligament by insertion through a small transverse incision along the wrist, in accordance with the present invention, comprises a blade having an arch-shaped configuration in cross-section which arch becomes generally flat at a tip section of the blade. The tip is tapered in plan view and adapted to be initially inserted through the incision to facilitate advancement of the blade along a plane between the ligament and overlying structures to thereby progressively expose the ligament by distal retraction. A light conduit extends through the arch of the blade and terminates in spaced relation to the tip to project light towards the tip to illuminate the area being distally retracted between the tip and conduit.

The light conduit is preferably a fiber optic cable.

The blade may be formed with a finger gripping portion projecting upward from the arch-shaped portion containing the tip. This finger gripping portion can form an angle with the blade portion of between 80°–100°. The cable preferably extends along the finger gripping portion and bends through a predetermined angle to extend through the arch-shaped cross-section of the blade portion.

In accordance with a further feature of this invention, the cable is substantially circular in cross-section and gradually assumes an ovaloid or elliptical cross-section toward the tip to avoid visual obstruction. A minor axis of the ovaloid or ellipsoid is in the vertical direction of the arch.

The tip is preferably spade-shaped in plan view. In combination with the arch-shaped cross-section of the blade, the resulting configuration facilitates the advancement of the tip through the plane between the ligament and overlying structures while lifting the overlying structures away from the ligament to progressively expose it for cutting with conventional cutting instruments. The direct illumination of the arch enables easy identification of the median nerve during cutting to prevent damage thereto.

The arch-shaped blade includes a pair of walls defining the arch which are connected together at the top of the arch with a smoothly rounded wall portion. The two walls preferably form an angle at the apex of between 45°-90°. Each wall, viewed in cross-section, preferably extends for a distance of about 1-1.5 cm.

The finger gripping portion is also preferably arch-shaped in cross-section and this arch receives the cable which may project therealong and above the retractor. A connector, such as a fiber optic bundle connector, may be disposed at the uppermost end of the cable to facilitate connection to a light source. The upper end of the finger gripping portion may be curved forwardly and downwardly from the upper end of the cable and toward the tip to receive at least one of the surgeon's fingers to facilitate lifting of the tip and distal retraction during surgery.

A method of surgically releasing the carpal ligament is also disclosed. The method comprises the steps of initially forming a transverse incision in a crease of the skin in the patient's wrist. The tip of a retractor is then inserted through the incision and caused to advance along a plane formed between the carpal ligament and overlying structure such as the palmaris brevis muscles, fascia and superficial palmar arch (vessel) and fat. As the tip is advanced through the plane, the overlying structure is progressively distally retracted from the carpal ligament by the arch-shaped cross-section of the retracting blade extending through the plane. A light source emitted from a cable extending through the arch and terminating within the arch provides illumination of the distally retracted area and thereby the ligament to enable progressive and complete splitting of the ligament with a conventional cutting instrument as the blade of the retractor continues to advance along the length of the ligament toward the middle of the palm of the hand. Thereafter, the retractor is withdrawn through the incision.

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BRIEF DESCRIPTION OF THE DRAWINGS

FIG. 11 is a sectional view taken through a patient's wrist to depict the carpal tunnel and surrounding structures as well as the carpal ligament;

BEST MODE FOR CARRYING OUT THE INVENTION

FIG. 11 is a sectional view of a patient's wrist W depicting the carpal tunnel C which is defined by a dorsal floor or base formed by a concave arch of carpal bones B covered by intrinsic and extrinsic palmar wrist ligaments. The roof of the tunnel C is formed by a transverse carpal ligament L. Palmaris Brevis P and a layer of fatty tissue F and skin S cover the ligament L. The ulnar nerve N and artery extends along one side of the ligament L as shown and plural flexor tendons T extend through the carpal tunnel C into the patient's hand H. The median nerve M is located within the tunnel immediately beneath the carpal ligament L.

Figure 12:
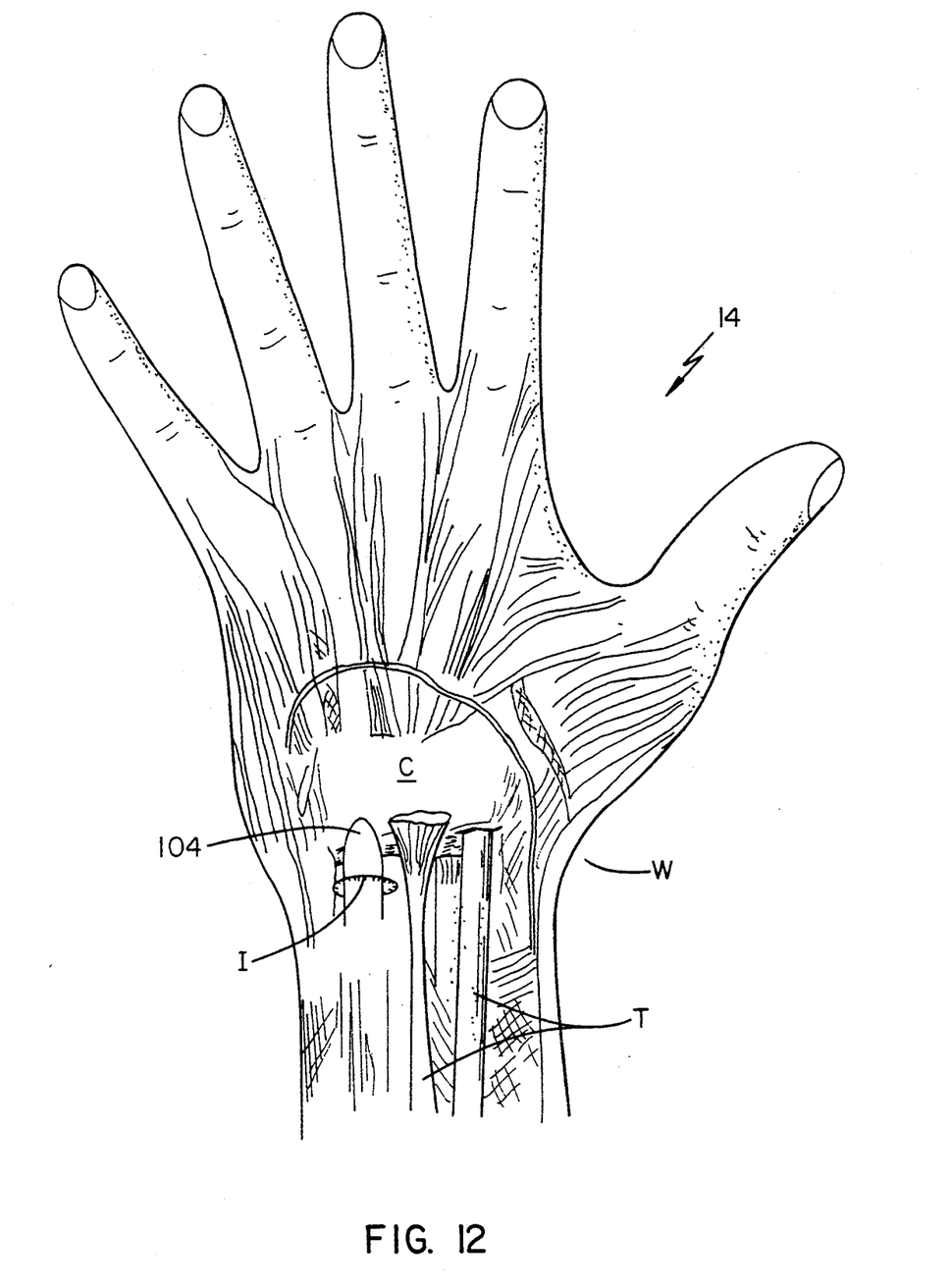
FIG. 12 is a top plan view, partly in section, of a patient's hand depicting the relative locations of the initial wrist incision and the transverse carpal ligament to be released.
Figure 13:
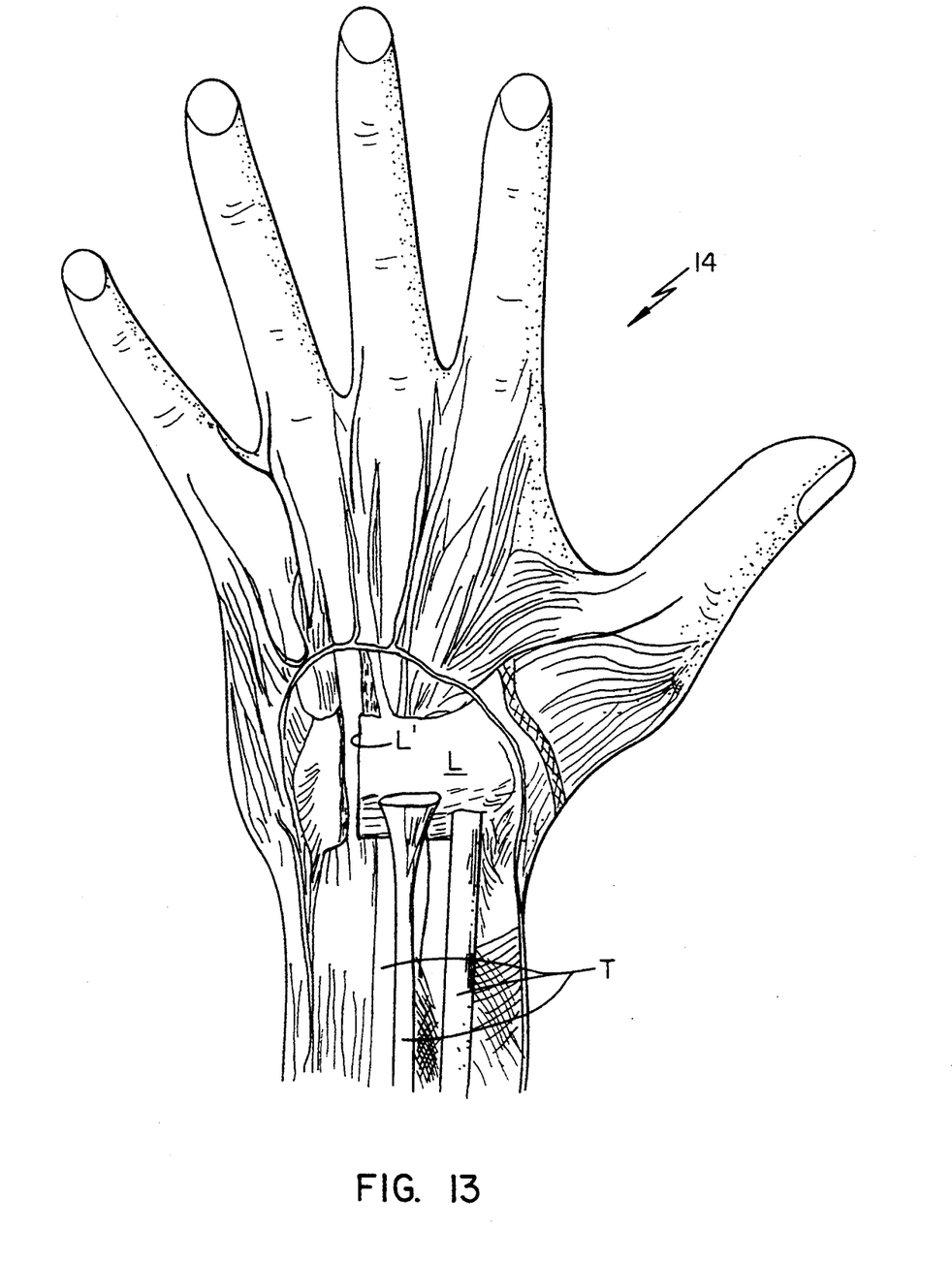
FIG. 13 is a view similar to FIG. 12 after release of the carpal ligament.

To decompress the tunnel C, it is preferable, from the patient's standpoint, for the surgeon to make a small transverse incision I in a skin crease in the patient's wrist W as depicted in FIG. 12, and to then use a conventional cutting instrument (not shown) which is inserted through the incision to completely cut and divide the transverse carpal ligament L with a longitudinal incision L' as depicted in FIG. 13. However, due to the location of the transverse incision I, it is extremely important to adequately expose and illuminate the carpal ligament L to ensure cutting only of the ligament without cutting arteries or the median nerve M or tendons T within the tunnel C.

Figure 1:
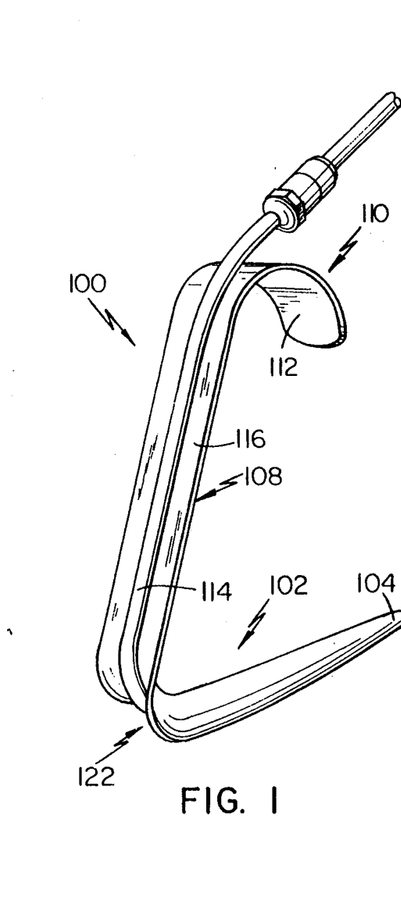
FIG. 1 is a perspective view of the retractor according to the present invention.
Figure 2:
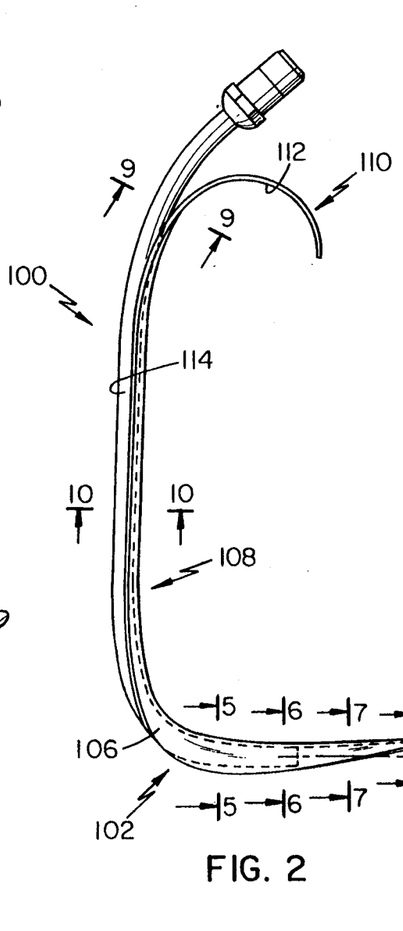
FIG. 2 is a side elevational view of the retractor of FIG. 1.
Figure 2:
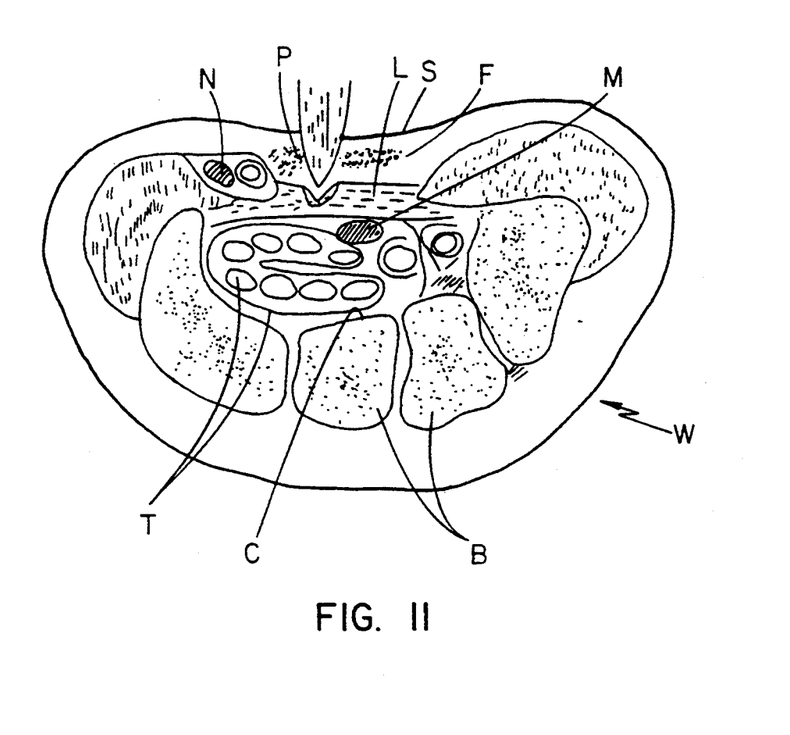
Figure 3:
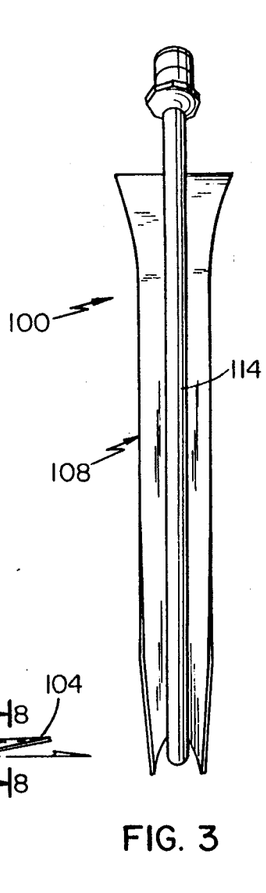
FIG. 3 is a rear elevational view of the retractor.
Figure 4:
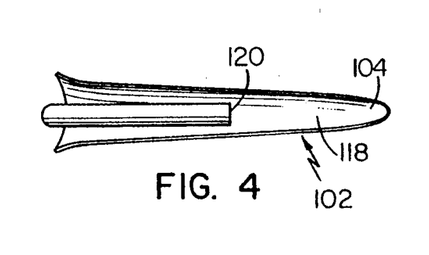
FIG. 4 is a bottom plan view of the retractor.

To achieve these foregoing objects, the surgical retractor or CARPOSCOPE TM 100 of the present invention depicted in FIGS. 1 and 2 comprises a blade shaped portion 102 having an arch-shaped configuration as depicted in FIGS. 5-8 which becomes progressively flatter toward the tip section 104 which is substantially flat (see e.g., FIG. 8) and spade-shaped in plan view (see FIG. 4). Projecting upwardly from the root 106 of the blade portion 102 at an angle of about 80°-100° is a finger gripping portion 108 of sufficient length to enable the surgeon to position his fingers therearound to control the retractor 100. The upper end 110 of the finger gripping portion curves forwardly and downwardly to define a stop surface 112 along its underside against which the surgeon's index finger rests to impart a lifting force to the retractor 100 during use to facilitate distal retraction of the tip section 104 as discussed more fully below.

Figure 10:
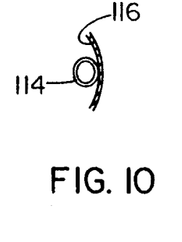
FIG. 10 is a sectional view taken along the line 10—10 of FIG. 2.

The finger gripping portion 108 is also somewhat arch-shaped in cross-section (FIGS. 4 and 10) and a fiber optic conduit 114 runs through the resulting concave groove 116 along the finger gripping portion 108 and thence through a part of the concave groove 118 formed by the arched cross-section in the blade portion 102. The fiber optic conduit 114 is preferably of cylindrical cross-section along its run through the finger gripping portion 108 and then transitions to an oval cross-section (FIGS. 5 and 6) in the blade portion 102. As best depicted in FIG. 4, the tip 120 of the cable 114 is spaced from the tip section 104 to enable illumination of the area between the fiber optic cable tip and the blade tip section 104 during the surgical procedure. There is a clearance 122 between the underside of the ovaloid fiber optic cable in the blade portion 102 and the lowermost surfaces 126 of the walls 124 forming the arched cross-section (see e.g., FIGS. 5 and 6) to allow the surgeon to sight through the incision I and along this clearance 122 as he or she guides the retractor 100 along the top of the transverse carpal ligament L to easily identify the ligament and surrounding nerves M to enable precise and complete cutting of the ligament. Thus, this oval shape advantageously reduces visual obstruction while providing excellent illumination.

The feature of forming the blade portion 102 with arch-shaped walls 124 is important to facilitate retraction of subcutaneous tissue (such as fat F and muscle) away from the carpal ligament L to improve the visual field. Without this configuration, i.e., if the entire blade portion 102 is flat, the subcutaneous tissue extrudes into the field and causes poor exposure and extreme difficulty in performing the release procedure. The spade-shape of the tip section 104 is also important to facilitate advancement of the blade portion 102 through the plane P between the carpal ligament L and overlying structures such as the palmaris brevis muscles, facia and superficial palmar arch and fat F. The tip section 102 easily slides along the top of the ligament L and the arch-shaped walls 124 contribute to the distal retraction of the overlying structure away from the ligament L to enable progressive cutting or splitting of the ligament with conventional cutting instruments (e.g., scissors, knife, etc.) as the blade portion 102 of the retractor 100 continues to advance until the entire ligament is split near the middle of the palm of the hand.

Figure 5:
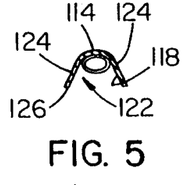
FIG. 5 is a sectional view taken along the line 5—5 of FIG. 2.
Figure 6:
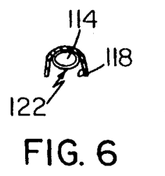
FIG. 6 is a sectional view taken along the line 6—6 of FIG. 2.
Figure 7:
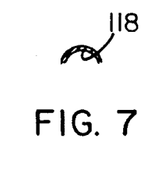
FIG. 7 is a sectional view taken along the line 7—7 of FIG. 2.
Figure 8:
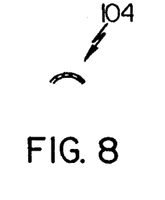
FIG. 8 is a sectional view taken along the line 8—8 of FIG. 2.
Figure 9:
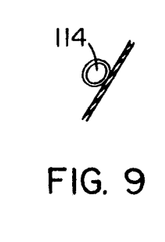
FIG. 9 is a sectional view taken along the line 9—9 of FIG. 2.

The arch-shaped walls 124 are preferably about 1-1.5 cm near the root section depicted in FIG. 5, then gradually taper down (decrease in width) towards the tip 104, and the walls preferably form an apex angle with each other of between 45°-90° which also flattens gradually towards the tip. The overall length C of the blade portion 102 is approximately 4-8 cm.

The fiber optic conduit 114 is preferably a protective metal sheath through which a fiber optic cable extends. The upper end of the sheath projecting above the upper end 110 of the finger gripping portion 108 terminates in a fiber optic connector which is conventional and adapted for quick disconnect connection to a fiber optic cable.

Another preferred surgical procedure for releasing the carpal tunnel with the surgical retractor 100 of the present invention is as follows. First, under pneumatic tourniquet control, a 1.5 cm long transverse incision is made from the mid-point of the flexion crease of the wrist towards the pisiform. Next, using a scissors spreading technique, the skin incision is deepened and two carpal tunnel access retractors are inserted to expose the forearm fascia superiorly. The fascia is incised by about 2 cm with a knife or scissors.

Figure 20:
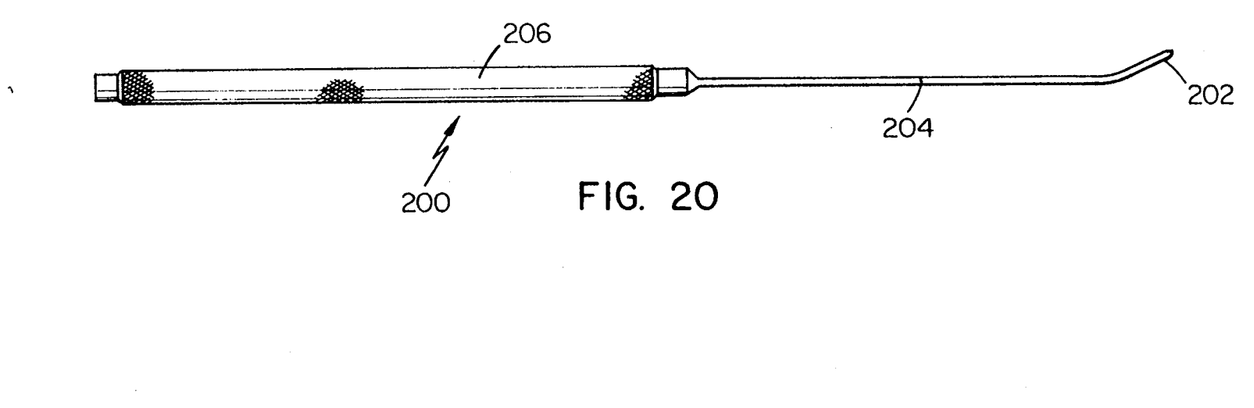
FIG. 20 is a side plan view of a carpal tunnel dissector constructed in accordance with a further feature of my present invention.
Figures 21, 22:
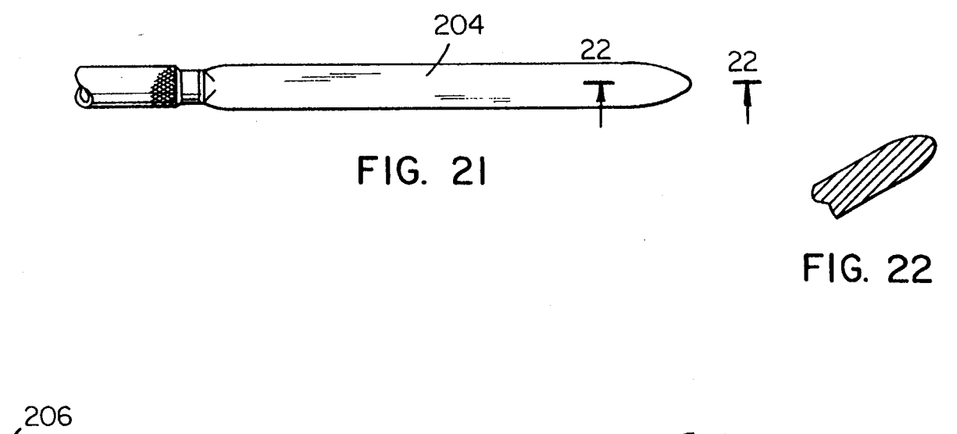
FIG. 21 is a top plan view of the dissector of FIG. 20.
FIG. 22 is a view taken along the line 22—22 of FIG. 20.

The dissection of the Synovium then occurs. In accordance with a further feature of the present invention, a carpal tunnel dissector 200 as depicted in FIGS. 20-22 is inserted through the fascial incision superiorly by about 1 to 2 cm, then inferiorly through the carpal tunnel towards the base of the ring finger until the elevated tip 202 of the dissector 200 is palpable through the palmar skin immediately below the distal margin of the ligament. A pair of conventional access retractors (not shown) previously inserted through the incision are removed at this time. As the dissector tip 202 is being advanced inferiorly, the surgeon should hug and feel the washboard-like undersurface of the ligament. The elevated tip 202 projects at an angle of approximately 25° from an elongate blade portion 204 connected to a handle 206. The blade portion 204 is slightly bendable and the tip 202 has a ski shape as best depicted in FIG. 22 for easy dissection of the carpal tunnel.

Figures 14, 15, 16, 17, 18, 19:
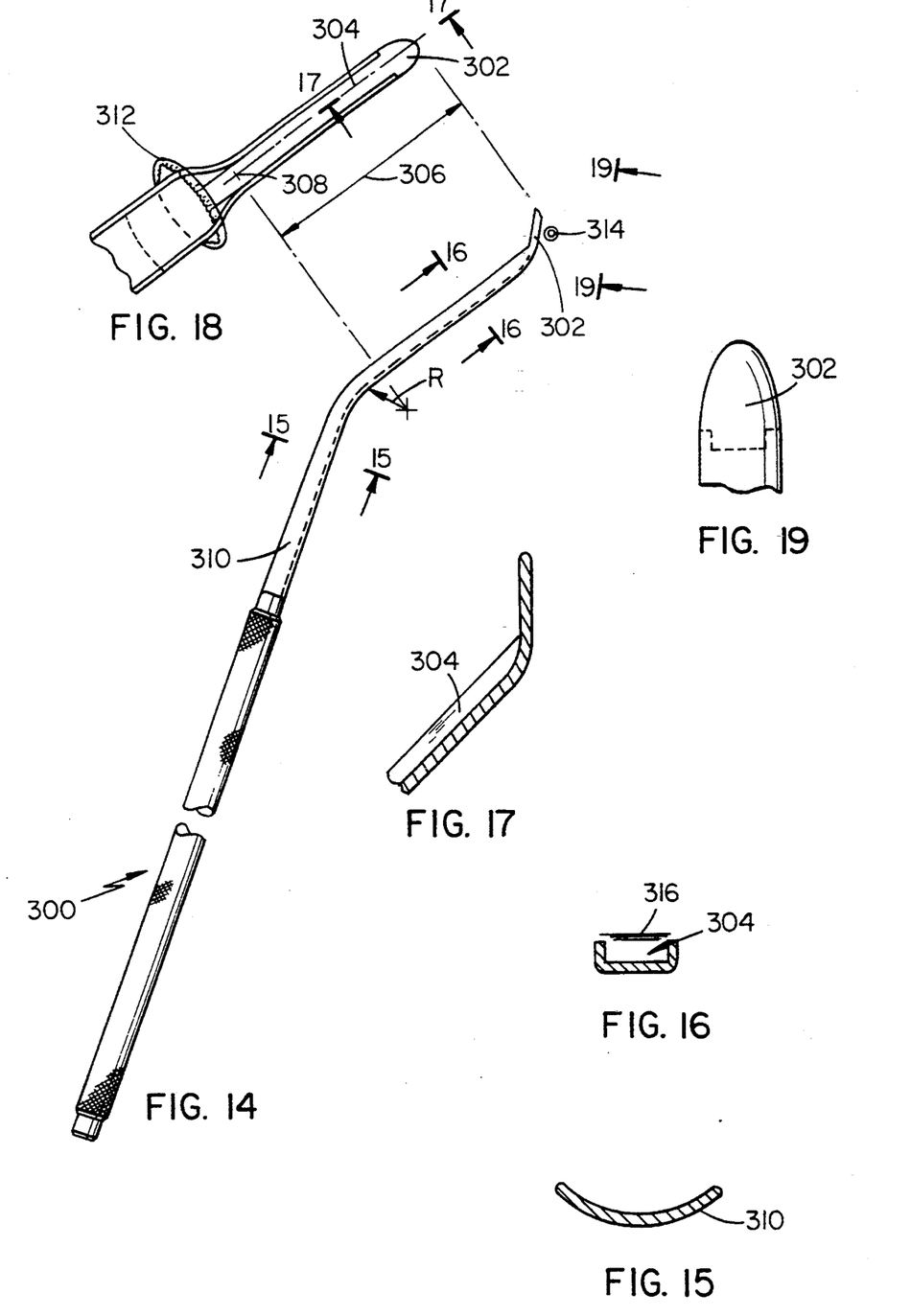
FIG. 14 is a side view of a carpal tunnel guider used in conjunction with the retractor or CARPOSCOPE TM of my invention.
FIG. 15 is sectional view taken along the line 15—15 of FIG. 14.
FIG. 16 is a sectional view taken along the line 16—16 of FIG. 14.
FIG. 17 is a sectional view taken along the line 17—17 of FIG. 18.
FIG. 18 is a top plan view of a working end of the carpal tunnel guider of this invention.
FIG. 19 is a view taken along the lines 19—19 of FIG. 14.

Next, a carpal tunnel guider 300 as depicted in FIGS. 14-19 constructed in accordance with the present invention is inserted into the tunnel by sliding its tip 302 under the dissector as this is being removed. The surgeon can feel the tip 302 of the guider 300 through the skin below the distal margin of the ligament. The retractor 100 and the tip section 104 thereof is then inserted into the wound by placing the tip section on top (volar) of the ligament. At this time, the ligament is sandwiched between the retractor 100 and the guider 300. With the non-dominant hand of the surgeon suspending the handle, the retractor 100 is advanced by "walking" its tip on the ligament towards the ring finger as the ligament is being incised with a knife and/or scissors using the dominant hand following the trough 304 of the guider 300. This trough section 304 is best depicted in FIGS. 16-18 of the drawing. The surgeon will feel the ligament "give" as the last portion of it is being cut. Following, the guider 300 is removed and the tunnel is inspected for completeness of release and condition of the median nerve by means of the retractor 100. The skin incision is then repaired to complete the procedure.

The carpal tunnel guider 300 of this invention therefore constitutes an improvement feature having a design which uniquely lends itself to use with the retractor 100 of this invention. The outside surfaces of the guider 300 are preferably polished and the inside surfaces are in a matte finish to reduce glare from the fiberoptic light of the retractor 100. The working length 306 of the guider 300 is defined by the trough 304 (FIG. 16) which is a rectangular channel in cross-section having a length slightly longer than the carpal tunnel. The proximal end portion of the trough 304 as at point 308 defines the beginning of the handle 310 which is located outside of the incision during the procedure. The skin incision is schematically depicted at 312 in FIG. 18. The tip 302 of guider 300 is elevated at an angle of approximately 45°

(FIG. 17) relative to the trough section 304 and this tip orientation helps in the dissection of the carpal tunnel and protects the palmar arch (schematically depicted in FIG. 14 at 314) from being cut.

The trough 304 advantageously provides clearance for the ligament since it is under the ligament, wherein the ligament 316 is schematically depicted in FIG. 16. Finally, the handle portion 310 as best depicted in FIG. 15 is slightly hollow or grooved to provide a shape which gives some added visual field towards the tunnel.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

I claim:

1. A palmar structure surgical retractor for exposing a carpal ligament through a small transverse incision along the wrist in the performance of surgery to release the carpal ligament, comprising:

an elongated blade having a proximal end and a distal tip section, said proximal end having an arch-shaped configuration in cross-section, said arch-shaped configuration becoming progressively flatter towards, and generally flat at, said tip section, said tip section being tapered and spade-shaped in plan view to enable it to be initially inserted through the transverse incision to facilitate advancement of the blade along a plane between the carpal ligament and overlying skin and tissue and muscle structures to thereby progressively expose the ligament by distal retraction;

a finger gripping portion extending substantially perpendicularly from said proximal end of said blade, said finger gripping portion having an arch-shaped configuration in cross-section which is continuous with said arch-shaped configuration of said blade; and a light conduit extending through the continuous arch of said blade and said finger gripping portion and terminating in spaced relation to said tip section so as to project light toward said tip section to illuminate the area being distally retracted between said tip section and said light conduit.

2. The retractor of claim 1, wherein said light conduit is a fiber optic cable.

3. The retractor of claim 2, wherein said cable is substantially circular in cross-section and gradually assumes an ovaloid or elliptical cross-section toward said section to avoid visual obstruction.

4. The retractor of claim 3, wherein a minor access of the ovaloid or ellipsoid is in the vertical direction of the arch.

5. The retractor of claim 1, wherein the arch-shaped blade includes a pair of walls defining the arch which are connected together at the top of the arch with a smoothly rounded wall portion.

6. The retractor of claim 5, wherein said pair of walls form an angle at the apex of the arch between about 45°–90° adjacent said proximal end of said blade.

7. The retractor of claim 6, wherein each wall adjacent said proximal end of said blade, viewed in cross-section, extends for a distance of approximately 1–1.5 cm.

8. The retractor of claim 5, wherein said finger gripping portion has a proximal end which is curved forwardly and downwardly toward said tip section to receive at least one of the surgeon's fingers to facilitate lifting of the tip during surgery.

9. The retractor of claim 8, wherein the finger gripping portion and the arch-shaped portion form an angle of about 80°–100° therebetween.

* * * * *